US007078724B2

(12) United States Patent
Kirchmeyer et al.

(10) Patent No.: US 7,078,724 B2
(45) Date of Patent: Jul. 18, 2006

(54) ORGANIC COMPOUNDS HAVING A CORE-SHELL STRUCTURE

(75) Inventors: Stephan Kirchmeyer, Leverkusen (DE); Sergei Ponomarenko, Moskau (RU)

(73) Assignee: H.C. Starck, GmbH, Goslar (DE)

( * ) Notice: Subject to any disclaimer, the term of this patent is extended or adjusted under 35 U.S.C. 154(b) by 0 days.

(21) Appl. No.: 10/661,436

(22) Filed: Sep. 12, 2003

(65) Prior Publication Data

US 2004/0132959 A1 Jul. 8, 2004

(30) Foreign Application Priority Data

Sep. 13, 2002 (DE) ............................ 102 42 715
Feb. 12, 2003 (DE) ............................ 103 05 945

(51) Int. Cl.
*H01L 29/08* (2006.01)
*H01L 23/58* (2006.01)

(52) U.S. Cl. ........................... 257/40; 257/642
(58) Field of Classification Search ................ 257/40, 257/633–636, 642, 643
See application file for complete search history.

(56) References Cited

U.S. PATENT DOCUMENTS

| 4,435,548 | A | 3/1984 | Tomalia ............... 525/451 |
|---|---|---|---|
| 4,507,466 | A | 3/1985 | Tomalia et al. ......... 528/332 |
| 4,631,337 | A | 12/1986 | Tomalia et al. ......... 528/391 |
| 5,070,183 | A | 12/1991 | Kim .................. 528/397 |
| 5,145,930 | A | 9/1992 | Kim .................. 528/4 |
| 5,183,862 | A | 2/1993 | Figuly ............... 525/437 |
| 5,225,522 | A | 7/1993 | Turner et al. .......... 528/361 |
| 5,264,543 | A | 11/1993 | Kim .................. 528/331 |
| 5,270,402 | A | 12/1993 | Figuly ............... 525/440 |
| 5,346,984 | A | 9/1994 | Hasegawa ............. 528/323 |
| 6,025,462 | A | 2/2000 | Wang et al. ........... 528/377 |
| 6,384,172 | B1 | 5/2002 | Dvornic et al. ........ 528/15 |

FOREIGN PATENT DOCUMENTS

| WO | 01/59030 | 8/2001 |
|---|---|---|
| WO | 02/26859 | 4/2002 |

OTHER PUBLICATIONS

Nature, vol. 401, Oct. 14, 1999, H. Sirringhaus et al., "Two-dimensional charge transport in self-organized, high-mobility conjugated polymers", pp. 685-688.
Science, vol. 290, Dec. 15, 2000, H. Sirringhaus et al., "High-Resolution Inkjet Printing of All-Polymer Transistor Circuits", pp. 2123-2126.
Science, vol. 280, Jun. 12, 1998, "Integrated Optoelectronic Devices Based on Conjugated Poly-mers", pp. 1741-1744.
Chemistry of Materials, vol. 10, No. 2, Feb. 1998, H. E. Katz et al., "α-ω-Dihexyl-quaterthiophene: A Second Thin Film Single-Crystal Organic Semiconductor", pp. 457-459..
Synthetic Metals 101, (month unavailable) (1999), R. Azumi et al., "Thermal Behavior of α-Alkylated Oligothiophenes", pp. 544-545.
Science, vol. 290, Nov. 3, 2000, J. H. Schön et al., "A Light-Emitting Field-Effect Transistor" pp. 963-965.
Science, vol. 298, Nov. 1, 2002, Science's Compass, Retraction, J. H. Schön et al., pp. 961-965.
Chem. Mater., (month unavailabel) 1998, 10, H.E. Katz et al., "Synthesis, Solubility, and Field-Effect Mobility of Elongated and Oxa-Substituted α-ω-Dialkyl Thiophene Oligomers. Extension of "Polar Intermediate" Synthetic Strategy and Solution Deposition on Transistor Substrates", pp. 633-638.
Advances in Dendritic Macromolecules, vol. 2, (month unavailable) 1995, L.J. Mathais et al., "Silicon-Based Stars, Dendrimers, and Hyperbranched Polymers", pp. 101-121.
Kim, Y.H. et al: "Hyperbranched Polyphenylenes" Macromolecules, American Chemical Society. Easton, US, Bd. 25, Nr. 21, (Oct. 12, 1992), Seiten 5561-5572, XP000315427 ISSN: 0024-9297 "Seite 5562, Spalte 1—Seite 5570, Spalte 1".
Kiebooms R et al: "Synthesis, Electrical, and Optical Properties of Conjugated Polymers" Handbook of Advanced Electronic and Photonic Materials and Devices, XX, XX, Bd. 8, 2001, Seiten 1-102, XP001029240 "das ganze Dokument".
Star-Shaped Oligothiophenes for Solution-Processible Organic Field-Effect Transistors, Adv. Funct. Mater, 2003, 13, No. 8, Aug., © Wiley-VCH Verlag GmbH & Co. KGaA, Weinheim, pp. 591-596.

*Primary Examiner*—Hung Vu
(74) *Attorney, Agent, or Firm*—Joseph C. Gil

(57) ABSTRACT

The invention relates to compounds having a core-shell structure, to a process for preparing them and to their use as semiconductors in electronic components.

15 Claims, No Drawings

ORGANIC COMPOUNDS HAVING A CORE-SHELL STRUCTURE

BACKGROUND OF THE INVENTION

1. Field of the Invention

The invention relates to organic compounds having a core-shell structure, to a process for preparing them and to their use as semiconductors in electronic components.

2. Brief Description of the Prior Art

The field of molecular electronics has developed rapidly in the last 15 years with the discovery of organic conductive and semiconductive compounds. In this time, many compounds which have semiconductive or electrooptical properties have been found. While it is generally accepted that molecular electronics will not displace conventional semiconductor building blocks based on silicon, it is believed that molecular electronic components will open up new applications in which suitability for coating large areas, structural flexibility, processability at low temperatures and low costs are required. Semiconductive organic compounds are at present being developed for applications such as organic field effect transistors (OFETs), organic luminescence diodes (OLEDs), sensors and photovoltaic elements. Simple structuring and integration of OFETs into integrated organic semiconductor circuits make it possible to achieve inexpensive solutions for smart cards or price signs which have hitherto not been realized with the aid of silicon technology, owing to the price and the lack of flexibility of the silicon building blocks. Likewise, OFETs can be used as circuit elements in large-area flexible matrix displays. An overview of organic semiconductors, integrated semiconductor circuits and their uses is given, for example, in Electronics 2002, volume 15, p. 38. A field effect transistor (FET) is a three-electrode element in which the conductivity of a thin conduction channel between two electrodes (known as "source" and "drain") is controlled by means of a third electrode (known as the "gate") separated from the conduction channel by a thin insulating layer. The most important characteristic properties of a field effect transistor are the mobility of the charge carriers, which has a critical effect on the switching speed of the transistor, and the ratio of the currents in the switched-on and switched-off state, known as the "on/off ratio". Two large classes of compounds have hitherto been used in organic field effect transistors. All these compounds have long conjugated units and are classified into conjugated polymers and conjugated oligomers on the basis of the molecular weight and structure. Oligomers generally have a uniform molecular structure and a molecular weight of less than 10 000 dalton. Polymers generally consist of chains made up of uniform repeating units and having a molecular weight distribution. However, there is a continuous transition between oligomers and polymers. The distinction between oligomers and polymers is frequently made to reflect the fact that there is a fundamental difference in the processing of these compounds. Oligomers are frequently vaporizable and are applied to substrates by vapour deposition processes. The term polymers is frequently used to refer to compounds which are no longer vaporizable and are therefore applied by other methods, regardless of their molecular structure. It is generally desirable for polymers to be soluble in a liquid medium, for example organic solvents, and then be able to be applied by corresponding application methods. A very widespread application method is, for example, spin coating.

A particular elegant method is the application of semiconductive compounds by means of the inkjet process. In this process, a semiconductive solution is applied in the form of very fine droplets to the substrate and is dried. This method allows structuring to be carried out during application. A description of this method of applying semiconductive compounds is given, for example, in Nature, volume 401, p. 685. In general, the wet chemical methods are considered to have a greater potential for obtaining inexpensive integrated organic semiconductor circuits in a simple way.

An important prerequisite for the production of high-quality organic semiconductor circuits is compounds of extremely high purity. In semiconductors, ordering phenomena play an important role. Organic semiconductor circuits which have been constructed using compounds which are not of extremely high purity are generally unusable because they can hinder uniform alignment of the compounds. Hindering of a uniform alignment of the compounds and pronounced grain boundaries leads to a dramatic drop in the semiconductor properties. Also, residual impurities can, for example, inject charges into the semiconductive compound ("doping") and thus reduce the on/off ratio or act as charge scavengers and thus drastically reduce the mobility. Furthermore, impurities can initiate the reaction of the semiconductive compounds with oxygen and impurities having an oxidizing action can oxidize the semiconductive compounds and thus shorten possible storage, processing and operating lives.

The purities which are generally necessary are generally not achievable by known methods of polymer chemistry, e.g. washing, reprecipitation and extraction. On the other hand, oligomers as molecularly uniform and frequently volatile compounds can be purified relatively easily by sublimation or chromatography.

Some important representatives of semiconductive polymers are described below. Polyfluorenes and fluorene copolymers, for example poly(9,9-dioctylfluorene-co-bithiophene) (I)

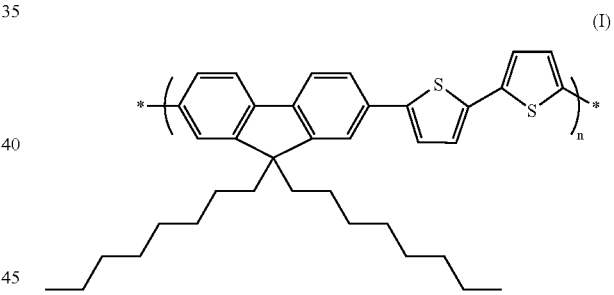

have been able to achieve charge mobilities, hereinafter also referred to as mobilities for the sake of brevity, of up to 0.02 $cm^2/Vs$ (Science, 2000, volume 290, p. 2123), and regio-regular poly(3-hexylthiophene-2,5-diyl) (II)

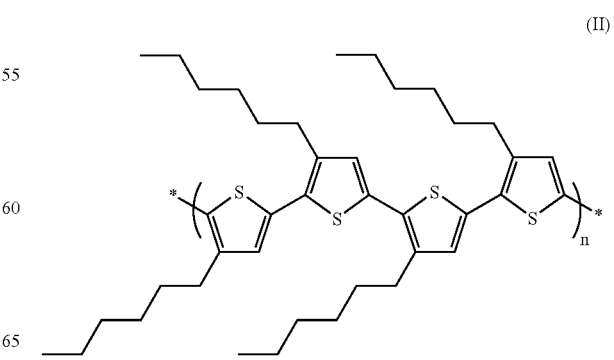

has even been able to achieve mobilities of up to 0.1 cm²/Vs (Science, 1998, volume 280, p. 1741). Polyfluorene, polyfluorene copolymers and poly(3-hexyl-thiophene-2,5-diyl), like virtually all long-chain polymers, form good films after application from solution and are therefore easy to process. However, as high molecular weight polymers having a molecular weight distribution, they cannot be purified by vacuum sublimation and only with difficulty by chromatography.

Important representatives of oligomeric semiconductive compounds are, for example, oligothiophenes, in particular those having terminal alkyl substituents as represented by the formula (III),

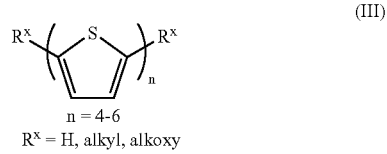

(III)

n = 4-6
$R^x$ = H, alkyl, alkoxy and pentacene (IV)

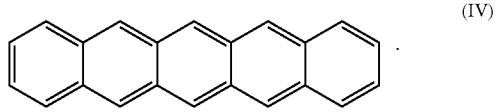

(IV)

Typical mobilities for, for example, α,α'-dihexyl-quarterthiophene, -quinquethiophene and -sexithiophene are 0.05–0.1 cm²/Vs.

Mesophases, in particular liquid-crystalline phases, appear to play an important role in semiconductive organic compounds, but this has hitherto not been fully understood by experts in the field. For example, the highest mobility has hitherto been reported for crystals of α,α'-dihexylquarterthiophenes (Chem. Mater., 1998, volume 10, p. 457), with these crystals crystallizing from an enantiotropic liquid-crystalline phase at a temperature of 80° C. (Synth. Met., 1999, volume 101, p. 544). Particularly high mobilities can be obtained when using single crystals, e.g. a mobility of 1.1 cm²/Vs has been described for single crystals of α,α'-sexithiophenes (Science, 2000, volume 290, p. 963). If oligomers are applied from solution, the mobilities usually drop considerably.

In general, the deterioration in the semiconductive properties when oligomeric compounds are processed from solution is attributed to the moderate solubility and low tendency to form films of the oligomeric compounds. Thus, inhomogeneities are attributed, for example, to precipitates formed from the solution during drying (Chem. Mater., 1998, volume 10, p. 633).

Attempts have therefore been made to combine the good processing and film-forming properties of semiconductive polymers with the properties of semiconductive oligomers. U.S. Pat. No. 6,025,462 describes conductive polymers having a star structure consisting of a branched core and a shell of conjugated side groups. However, these polymers have a number of disadvantages. If the side groups are formed by laterally unsubstituted conjugated structures, the resulting compounds are sparingly soluble or insoluble and cannot be processed. If the conjugated units are substituted by side groups, this does lead to an improved solubility but the side groups cause internal disorder and morphological disruptions as a result of the space they take up, resulting in impairment of the semiconductive properties of these compounds.

WO 02/26859 describes polymers having a conjugated backbone to which aromatic conjugated chains are attached. The polymers bear diarylamine side groups which make electron conduction possible. However, the diarylamine side groups make these compounds unsuitable as semiconductors.

There is therefore a continuing need for compounds which combine the properties of organic semiconductive oligomers and polymers.

It is therefore an object of the invention to provide organic compounds which can be processed from customary solvents and have good semiconductive properties. Such organic semiconductive compounds would be extremely suitable for coating large areas.

It would be desirable for the compounds to form high-quality layers of uniform thickness and morphology and to be suitable for electronic applications.

SUMMARY OF THE INVENTION

It has now surprisingly been found that organic compounds have the desired properties when they have a core-shell structure comprising a core made up of multifunctional units and a shell of linear conjugated oligomeric chains which are each kept at the terminal linkage point by a flexible nonconjugated chain.

The invention accordingly provides compounds which are characterized in that they have a core-shell structure comprising a core made up of multifunctional units and a shell of linear conjugated oligomeric chains which are each kept at the terminal linkage point by a flexible nonconjugated chain.

In a preferred embodiment, the compounds of the invention can be oligomers or polymers.

According to the invention, the core-shell structure is on a molecular level, i.e. it relates to the structure of one molecule.

For the purposes of the present invention, the terminal linkage point of the linear conjugated oligomeric chain is the point in the terminal unit of the linear conjugated oligomeric chain via which no further linkage to a further unit of this type occurs. The expression terminal is used in the sense of furthest away from the core.

DETAILED DESCRIPTION OF THE INVENTION

The compounds of the invention preferably have a core-shell structure of the formula (Z),

(Z)

where
K is an n-functional core,
L is a linear conjugated oligomeric chain,
R is a straight-chain or branched $C_2$–$C_{20}$-alkyl radical, a monounsaturated or polyunsaturated $C_2$–$C_{20}$-alkenyl radical, a $C_2$–$C_{20}$-alkoxy radical, a $C_2$–$C_{20}$-aralkyl radical or a $C_2$–$C_{20}$-oligoether or $C_2$–$C_{20}$-polyether radical, n is an integer greater than or equal to 3, preferably greater than or equal to 6.

The shell is formed by the n linear conjugated chains L kept by R.

Illustratively, if n is 3 or 6, these are structures of the formula (Z-3) or (Z-6)

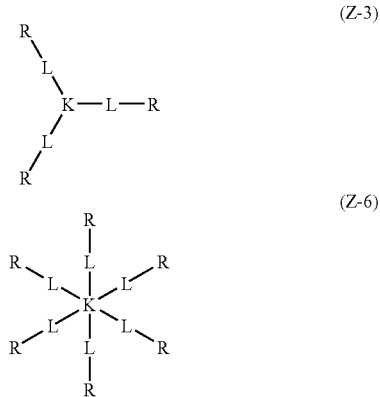

where K, L and R are as defined above.

In the structure of such compounds, a core made up of multifunctional units, i.e. a branched core, linear conjugated oligomeric chains and flexible nonconjugated chains are joined to one another.

The core made up of multifunctional units can have dendritic or hyperbranched structures.

Hyperbranched structures and their preparation are known per se to those skilled in the art. Hyperbranched polymers or oligomers have a particular structure which is determined by the structure of the monomers used. As monomers, use is made of $AB_n$ monomers, i.e. monomers which bear two different functions A and B. Of these, one function (A) is present only once per molecule while the other function (B) is present a plurality of times (n times). The two functions A and B can be reacted with one another to form a chemical bond, i.e. be polymerized. Owing to the monomer structure, the polymerization forms branched polymers having a tree-like structure, known as hyperbranched polymers. Hyperbranched polymers do not have regular branching points, no rings and virtually exclusively B functions at the ends of the chains. Hyperbranched polymers, their structure, the question of branching and the nomenclature is described for the example of hyperbranched polymers based on silicones in L. J. Mathias, T. W. Carothers, Adv. Dendritic Macromol. (1995), 2, 101–121, and the studies cited therein.

Preferred hyperbranched structures for the purposes of the invention are hyperbranched polymers.

However, the core made up of multifunctional units particularly preferably has dendritic structures since these are particularly well suited because of their regular make-up.

For the purposes of the invention, dendritic structures are synthetic macromolecular structures which are built up stepwise by in each case joining 2 or more monomers to each previously bound monomer, so that the number of monomer in groups grows exponentially with each step and a spherical tree structure is obtained in the end. This gives three-dimensional, macromolecular structures comprising groups which have branching points and extend in a regular fashion from a centre to the periphery. Such structures are usually built up layer by layer by methods known to those skilled in the art. The number of layers is usually referred to as generations. Both the number of branches in each layer and the number of terminal groups increase with each generation. Dendritic structures, methods of preparing them and nomenclature are known to those skilled in the art and described, for example, in G. R. Newkome et al., Dendrimers and Dendrons, Wiley-VCH, Weinheim, 2001.

The useful structures in the core made up of dendritic structures, hereinafter also referred to as dendritic core for short, are in principle those which are described in U.S. Pat. No. 6,025,462. These are, for example, hyperbranched structures such as polyphenylene, polyether ketones, polyesters, as are described, for example, in U.S. Pat. No. 5,183,862, U.S. Pat. No. 5,225,522 and U.S. Pat. No. 5,270,402, aramides as are described, for example, in U.S. Pat. No. 5,264,543, polyamides as described in U.S. Pat. No. 5,346,984, polycarbosilanes or polycarbosiloxanes as described, for example, in U.S. Pat. No. 6,384,172 or polyarylenes as described, for example, in U.S. Pat. No. 5,070,183 or U.S. Pat. No. 5,145,930, or dendritic structures such as polyarylenes, polyarylene ethers or polyamidoamines, as are described, for example, in U.S. Pat. No. 4,435,548 and U.S. Pat. No. 4,507,466, and also polyethylenimines as are described, for example, in U.S. Pat. No. 4,631,337.

However, other structural units can also be used for building up the dendritic core. The role of the dendritic core is predominantly to make available a number of different functions and thus to form a matrix to which the linear conjugated oligomeric chains are attached so as to produce a core-shell structure. The linear conjugated oligomeric chains are preordered by attachment to the matrix and their effectiveness is thus increased.

The dendritic core has a series of functionalities which are suitable for attachment of the linear conjugated oligomeric chains. According to the invention, both the dendritic core and the core made up of hyperbranched structures have at least 3, but preferably at least 6, different functionalities.

Preferred structures in the dendritic core are 1,3,5-phenylene units (formula V-a) and units of the formulae (V-b) to (V-e), with a plurality of identical or different units of the formulae (V-a) to (V-e) being linked to one another.

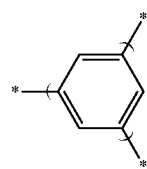

(V-a)

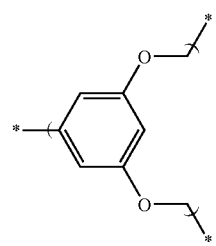

(V-b)

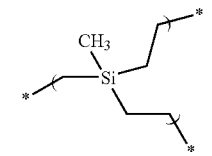

(V-c)

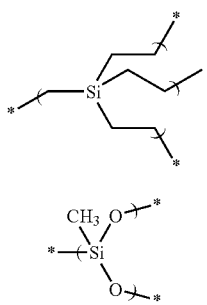
(V-d)

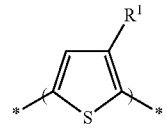
(V-e)

The positions marked by * in the formulae (V-a) to (V-e) and in the further formulae used below are the linkage points. The units (V-a) to (V-e) are linked via these to one another or to the linear conjugated oligomeric chains.

Examples of dendritic cores made up of units of the formula (V-a) are the following:

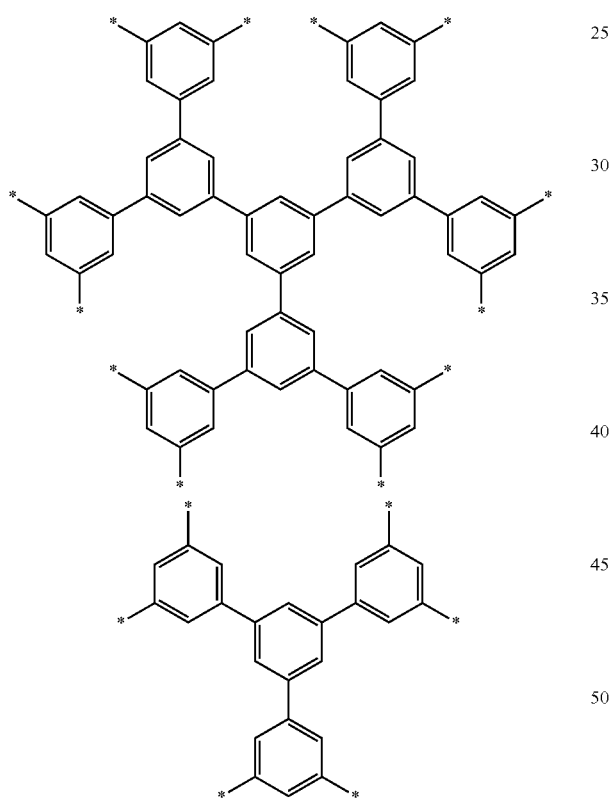

Linkage to the linear conjugated oligomeric chains occurs via the positions marked by *.

The shell of the compounds of the invention is formed by linear conjugated oligomeric chains which are joined to the core. Suitable linear conjugated oligomeric chains are in principle all chains having structures which are known as conductive or semiconductive oligomers or polymers. These are, for example, substituted or unsubstituted polyanilines, polythiophenes, polyethylenedioxy-thiophenes, polyphenylenes, polypyrroles, polyacetylenes, polyisonaphthenes, polyphenylenevinylenes, polyfluorenes, which can be used as homopolymers or homooligomers or as copolymers or cooligomers. Examples of such structures, which are preferably used as linear conjugated oligomeric chains, are chains made up of from 2 to 10, particularly preferably from 2 to 7, units of the formulae (VI-a) to (VI-e),

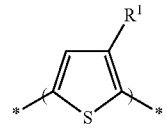
(VI-a)

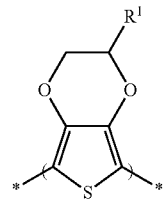
(VI-b)

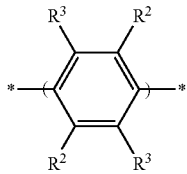
(VI-c)

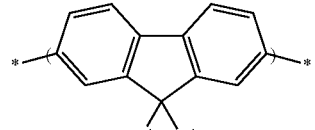
(VI-d)

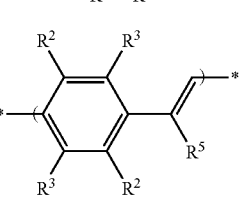
(VI-e)

where
$R^1$, $R^2$ and $R^3$ may be identical or different and are each hydrogen or a straight-chain or branched $C_1$–$C_{20}$-alkyl or $C_1$–$C_{20}$-alkoxy group, and are preferably identical and each hydrogen,
$R^4$ may be identical or different and are each hydrogen or a straight-chain or branched $C_1$–$C_{20}$-alkyl or $C_1$–$C_{20}$-alkoxy group, preferably hydrogen or a $C_6$–$C_{12}$-alkyl group, and
$R^5$ is hydrogen or a methyl or ethyl group, preferably hydrogen.

The positions marked by * in the formulae (VI-a) to (VI-e) are the linkage points via which the units (VI-a) to (VI-e) are linked to one another to form the linear conjugated oligomeric chain or at the ends of the chain are joined to the core or bear the flexible nonconjugated chain.

Linear conjugated oligomeric chains comprising units of substituted or unsubstituted 2,5-thiophenes (VI-a) or (VI-b) or substituted or unsubstituted 1,4-phenylenes (VI-c) are particularly preferably present. The above-mentioned numbers 2,5- or 1,4-indicate the positions via which linkage of the units occurs.

Very particular preference is given to linear conjugated oligomeric chains comprising units of unsubstituted 2,5-thiophenes (VI-a) or 2,5-(3,4-ethylenedioxy-thiophenes) (VI-b).

An example which may be mentioned is the compound of the formula (Z-6-1)

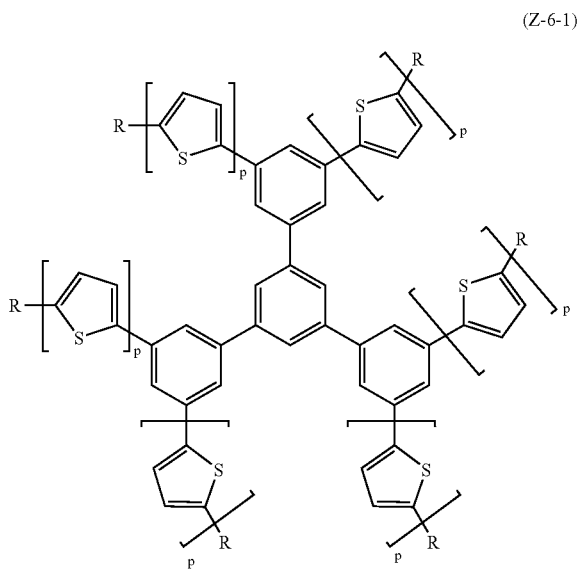

(Z-6-1)

where R is as defined for the formula (Z) and
p is an integer from 2 to 10, preferably from 2 to 7.

The linear conjugated oligomeric chains, denoted by R in the formula (Z), are each kept at the terminal linkage point by a flexible nonconjugated chain. Flexible chains are ones which have a high (intra)molecular mobility and as a result interact readily with solvent molecules and thus give improved solubility. For the purposes of the invention, flexible means (intra)molecularly movable. The flexible nonconjugated chains which are borne by the linear conjugated oligomeric chains at the terminal linkage point are likewise straight-chain or branched aliphatic, unsaturated or araliphatic chains which have from 2 to 20 carbon atoms, preferably from 6 to 20 carbon atoms, and may be interrupted by oxygen. Preference is given to aliphatic and oxyaliphatic groups, i.e. alkoxy groups or straight-chain or branched aliphatic groups which are interrupted by oxygen, e.g. oligoether or polyether groups. Particular preference is given to unbranched $C_2$–$C_{20}$-alkyl or $C_2$–$C_{20}$-alkoxy groups. Examples of suitable chains are alkyl groups such as n-hexyl, n-heptyl, n-octyl, n-nonyl, n-decyl and n-dodecyl groups and alkoxy groups such as n-hexyloxy, n-heptyloxy, n-octyloxy, n-nonyloxy, n-decyloxy and n-dodecyloxy groups.

Preferred embodiments of the present invention are compounds having structures having 1,3,5-phenylene units in the dendritic core, unsubstituted oligothiophene chains and oligo(3,4-ethylenedioxythiophene) chains having from 2 to 4 thiophene or 3,4-ethylenedioxythiophene units as linear conjugated oligomeric chains and $C_6$–$C_{12}$-alkyl groups as flexible nonconjugated chains.

The two compounds of the formulae (XII) and (XIII) may be mentioned by way of example:

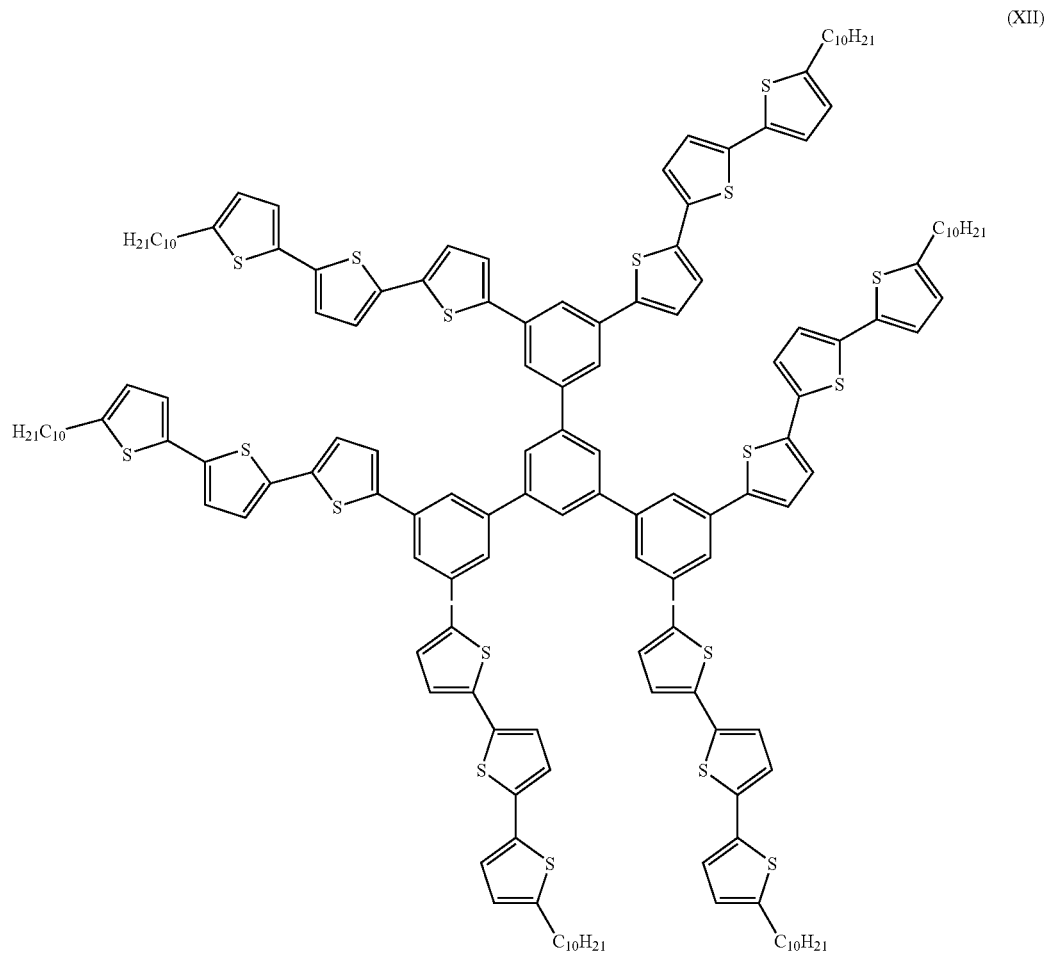

(XII)

-continued

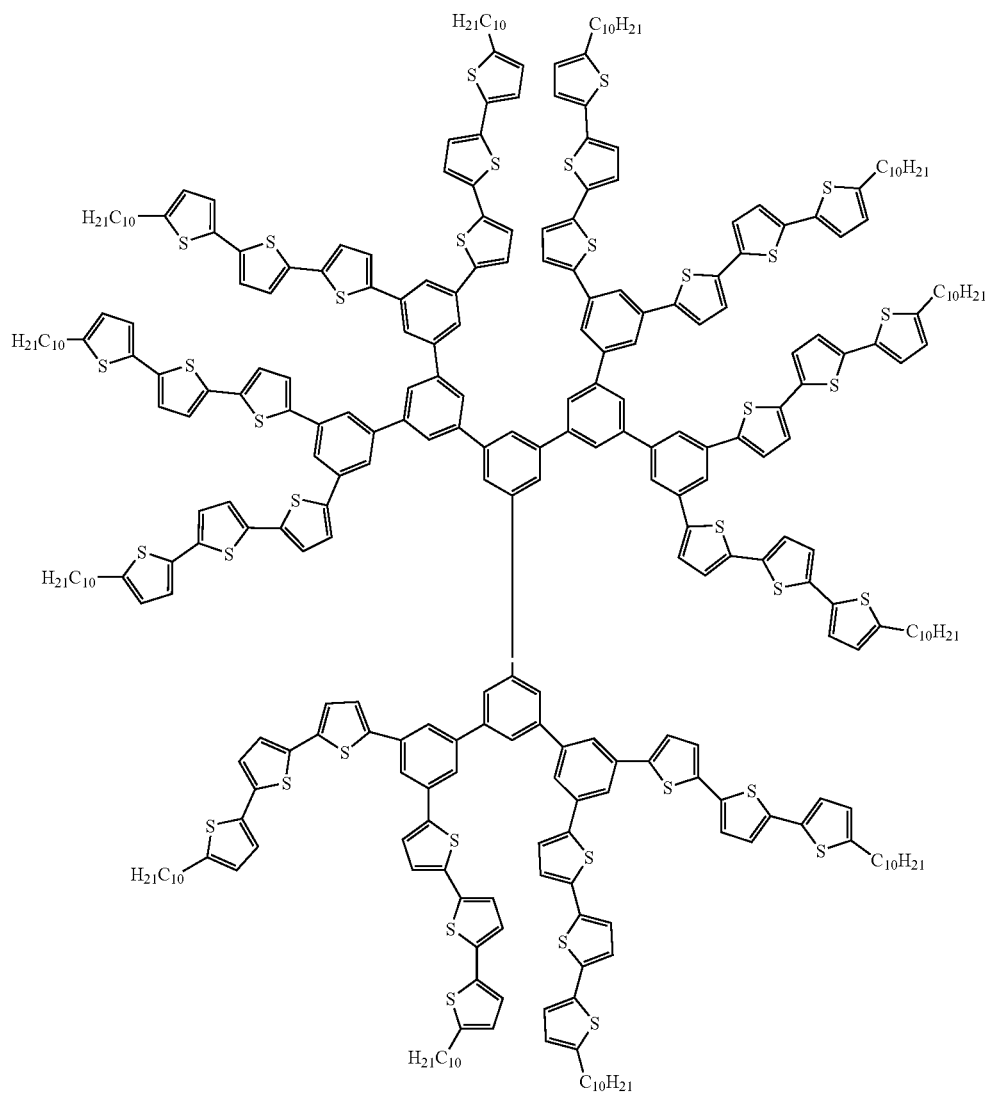

(XIII)

The compounds of the invention are conductive or semiconductive. Preferred compounds according to the present invention are compounds which are semiconductive. Particular preference is given to compounds which have mobilities of at least $10^{-4}$ cm$^2$/Vs The organic compounds of the invention are readily soluble in customary solvents such as chloroform, toluene, benzene, diethyl ether, dichloromethane or tetrahydrofuran and are thus very suitable for processing from solution. It is particularly surprising that compounds according to the invention having unsubstituted thiophene or 3,4-ethylenedioxythiophene units in the linear conjugated oligomeric chains display very good solubility without the internal order or morphology being disrupted by bulky side chains. Accordingly, the organic compounds of the invention possess good semiconductive properties and also excellent film-forming properties. They are therefore very suitable for a large-area coating. Furthermore, the organic semiconductive compounds of the invention have excellent thermal stability and good ageing behaviour.

The compounds of the invention can in principle be prepared by two different routes, which are referred to as the divergent and convergent methods of preparation.

In the convergent method of preparation, the linear conjugated oligomeric chain which is kept at one end by a nonconjugated flexible chain is prepared in a first step. In the case of a dendritic core, this is attached to a building block known as a monodendron, i.e. a building block which comprises part of the dendritic structure and can be joined to form a dendritic structure. In the last step of the preparation, a plurality of monodendra are combined to form the final structure.

In the divergent method of preparation, the dendritic core or the core comprising hyperbranched structures is prepared in the first step. The linear conjugated oligomeric chains which are each kept by a nonconjugated flexible chain can be attached to this core in a subsequent step.

In terms of the properties of the compounds of the invention, the method of preparation is in principle of no consequence. Within the methods of preparation described, a number of variants are possible. Thus, for example, it is possible to alter the order of the individual steps of the preparation and, for example, carry out the linking of the nonconjugated flexible chains to the linear conjugated oligomeric chains as the last step in the preparation.

However, depending on the structure to be produced, it can, for example, be useful to link the nonconjugated flexible chains to the linear conjugated oligomeric chains early in the preparation, since the flexible chains increase the solubility of the building blocks and thereby aid the preparation of the compounds of the invention.

A series of chemical reactions which are known in principle to those skilled in the art are available for building up the core made up of multifunctional units, for joining this to the linear conjugated oligomeric chains and for attaching the nonconjugated flexible chains to these. The chemical reactions carried out are preferably organometallic reactions. These have the advantage that they generally proceed under mild reaction conditions and highly selectively and give high reaction yields.

The invention therefore also provides a process for preparing the compounds of the invention, characterized in that these are prepared by organometallic reactions.

For organometallic reactions, it is necessary to introduce appropriate functions into the dendritic or hyperbranched core, the linear conjugated oligomeric chains and the flexible nonconjugated chains and subsequently to link these to one another.

Such functions are, for example, halogens for example chlorine, bromine and iodine, preferably bromine, organotin groups such as the trimethyltin or triethyltin group, organosilicon groups such as the trimethylsilane or triethylsilane group or organoboron groups such as boronic acids.

Particularly preferred organometallic reactions for coupling the individual components of the compounds of the invention are the Kumada coupling in which two bromo groups are coupled via Grignard compounds using palladium catalysts, e.g. 1,1-bis(diphenylphosphino)ferrocenedichloropalladium(II), and the Suzuki coupling in which boron-containing groups are coupled under basic conditions with bromo groups using palladium catalysts. The procedure for carrying out each of these coupling reactions is known to those skilled in the art.

The intermediates between the individual steps of the preparation and also the end compounds are preferably purified. This can be carried out by the known methods of distillation, sublimation, recrystallization, extraction, reprecipitation, washing or chromatography. Intermediates and final compounds are preferably purified by distillation, sublimation and chromatography, since these enable the highest purities to be obtained.

Compared with the known semiconductive polymers, this offers the advantage that the compounds of the invention can be prepared in high purities by means of simple, customary purification methods, thus making them suitable for use in semiconductor technology.

The compounds of the present invention can form mesophases (mesomorphic phases), i.e. physical phases between the solid and liquid state. These are also referred to as liquid-crystalline phases and aid preordering of the compounds of the invention. The compounds of the invention preferably form liquid-crystalline phases in the range from 50° C. to 300° C., very particularly preferably from 80° C. to 180° C.

The compounds of the invention are soluble to an extent of at least 0.1%, preferably at least 1%, particularly preferably at least 5%, in customary solvents, e.g. in chloroform, toluene, benzene, diethyl ether, dichloromethane or tetrahydrofuran.

The compounds of the invention form high-quality layers of uniform thickness and morphology from solution and are therefore suitable for electronic applications.

Finally, the invention also provides for the use of the compounds of the invention as semiconductors in electronic components such as field effect transistors, light-emitting components such as organic luminescence diodes or photovoltaic cells, lasers and sensors.

For these purposes, the compounds of the invention are preferably used in the form of layers.

To enable them to function effectively as semiconductors, the compounds of the invention have a sufficient mobility, e.g. at least $10^{-4}$ cm$^2$/Vs. For use, the compounds of the invention are applied to suitable substrates, for example to silicon wafers, polymer films or glass sheets provided with electrical or electronic structures. Application can in principle be carried out using all application methods. The compounds of the invention are preferably applied from a liquid phase, i.e. from solution, and the solvent is subsequently evaporated. Application from solution can be carried out by known methods, for example by spraying, dipping, printing and doctor blade coating. Particular preference is given to application by spin coating and by inkjet printing.

The layers of the compounds of the invention can be modified further after application, for example by thermal treatment, e.g. with transition through a liquid-crystalline phase, or for structuring, e.g. by laser ablation.

The invention further provides electronic components comprising the compounds of the invention as semiconductors.

This and other aspects of the invention are further described by way of the following non-limiting examples.

EXAMPLES

5-Decyl-2,2':5',2''-terthiophene (Synthesis, 1993, p. 1099; Chem. Mater., 1993, volume 5, p. 430) and (3,5-dibromophenyl)trimethylsilane (J. Organomet. Chem., 1983, volume 215, p. 149) were prepared by the known, cited procedures.

Example 1

Intermediate Comprising a Linear Conjugated Oligomeric Chain and Terminating Chain

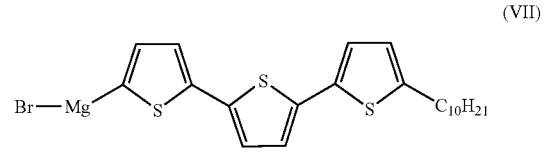

(VII)

Preparation of (5''-decyl-2,2':5',2''-terthien-5-yl)magnesium bromide (VII): Butyllithium (1.6 M n-BuLi in hexane, 8.8 ml, 14.0 mmol) is added dropwise via a syringe to a solution of 5-decyl-2,2':5',2''-terthiophene (6.60 g, 14.4 mmol) in abs. (absolute) THF (100 ml) at 2° C. while stirring under N$_2$. After the addition is complete, the solution is allowed to warm to room temperature (23° C.) and is stirred for another one hour. It is subsequently cooled back down to 2° C. and MgBr$_2$.Et$_2$O (3.67 g, 14.2 mmol) is added all at once. The reaction mixture is allowed to warm to room temperature again and is stirred for another one hour. (5''-Decyl-2,2':5',2''-terthien-5-yl)magnesium bromide is not isolated, but instead the solution obtained is used directly for the further reactions.

Example 2

Preparation of a Silane-Functional Monodendron Intermediate

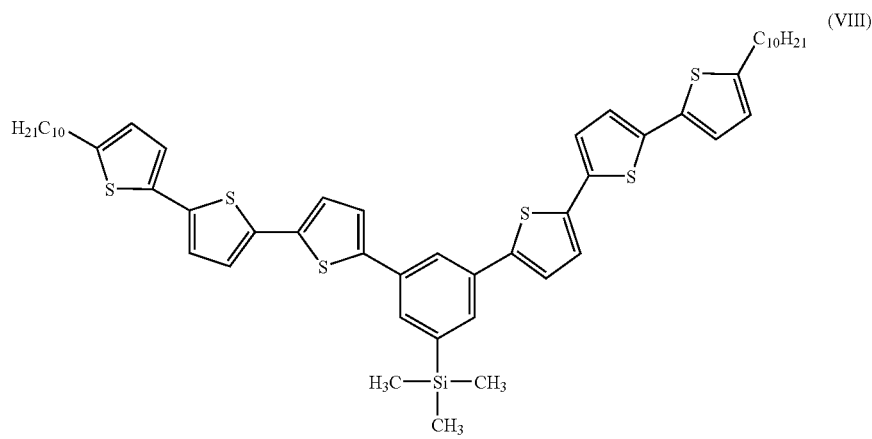

Preparation of [3,5-bis(5''-decyl-2,2':5',2''-terthien-5-yl)phenyl](trimethyl)silane (VIII): A freshly prepared solution of (5''-decyl-2,2':5',2''-terthien-5-yl)magnesium bromide (VII) (14.0 mmol) in abs. THF (Example 1) is added dropwise at room temperature to a solution of (3,5-dibromophenyl)trimethylsilane (1.54 g, 5 mmol) and Pd(dppf)Cl$_2$ (70 mg, 0.1 mmol) (dppf=diphenylphosphino) in 50 ml of abs. TBF. After the addition is complete, the solution is stirred for another two hours. The completeness of the reaction is monitored by TLC. The reaction mixture is subsequently poured into 300 ml of cold abs. diethyl ether and 200 ml of ice water containing 20 ml of 1 M (1 molar) HCl are added. The ether phase, which contains a yellow precipitate (the desired product), is separated off and washed with three 100 ml portions of ice water. The ether phase is filtered through a G3 glass filter, the product isolated is washed with three 50 ml portions of cold abs. diethyl ether and dried under reduced pressure. This gives 3.36 g of crude product in the form of dark yellow crystals. After purification by means of column chromatography (eluant: hexane/chloroform 4:1) at elevated temperature (40° C.) and subsequent recrystallization from hexane, 2.64 g of light-yellow crystals are obtained. Yield: 57%. Melting point: 120° C. $^1$H NMR (400 MHz, CDCl$_3$, TMS/ppm): 0.353 (s, 9H), 0.884 (t, 6H, J=6.9), 1.20–1.45 (overlapping peaks, 28 H), 1.688 (m, 4H, J=7.3, M=5), 2.798 (t, 4H, J=7.6), 6.692 (d, 2H, J=3.9), 6.996 (d, 2H, J=3.9), 7.021 (d, 2H, J=3.9), 7.109 (d, 2H, 3.9), 7.156 (d, 2H, 3.4), 7.287 (d, 2H, J=3.9), 7.623 (d, 2H, J=2.0), 7.763 (t, 1H, J=1.7).

Example 3

Preparation of a Boron-Functional Monodendron Intermediate

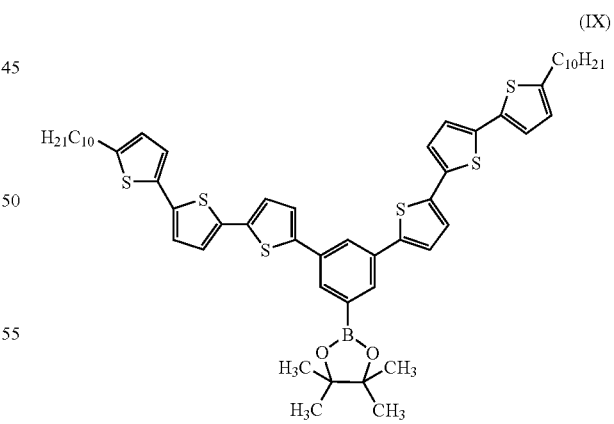

Preparation of 2-[3,5-bis(5''-decyl-2,2':5',2''-terthien-5-yl)phenyl]-4,4,5,5-tetramethyl-1,3,2-dioxaborolane (IX): A 100 ml three-neck round-bottom flask provided with reflux condenser, septum and protective gas inlet is filled with N$_2$ gas. The compound (VIII) (2.31 g, 2.5 mmol) and abs. tetrachloromethane (40 ml) are added. 5 ml of 1M BBr$_3$ solution in tetrachloromethane are subsequently added in one portion via the septum by means of a disposable polypropylene syringe and the reaction mixture is refluxed for 40 hours. The reaction mixture is subsequently cooled to room temperature and transferred by means of a syringe into a 500 ml conical flask containing 250 ml of 1 M NaOH solution. 200 ml of water are then added, the mixture is stirred vigorously and the aqueous phase is decanted off. The wet salt which remains is suspended in a mixture of diethyl ether (200 ml), THF (100 ml) and 2 M HCl (300 ml) and the mixture is stirred vigorously for 3 hours until two phases are formed. The ether phase is separated off and the aqueous phase is washed with diethyl ether. The combined ether phases are washed with three 100 ml portions of water and dried over $Na_2SO_4$. The solvent is removed on a rotary evaporator. This gives 4 g of wet boronic acid derivative in the form of a brown solid to which pinacol (330 mg, 2.75 mmol) and abs. toluene (100 ml) are added. The mixture is refluxed overnight using a Dean-Stark apparatus (water separator). After cooling and removal of the toluene on a rotary evaporator, 3 g of crude product are obtained in the form of a brown solid. Purification by means of column chromatography (eluant: toluene) gives 1.49 g of clean product as a dark yellow solid. Yield: 61%. $^1$H NMR (400 MHz, $CDCl_3$, TMS/ppm): 0.884 (t, 6H, J=6.9), 1.20–1.45 (overlapping peaks, 28 H), 1.388 (s, 12H), 1.688 (m, 4H, M=5, J=7.5), 2.798 (t, 4H, J=7.6), 6.692 (d, 2H, J=3.4), 6.995 (d, 2H, J=3.4), 7.071 (d, 2H, J=3.9), 7.104 (d, 2H, 3.9), 7.148 (d, 2H, 3.9), 7.334 (d, 2H, 3.4), 7.868 (t, 1H, J=1.7), 7.935 (d, 2H, J=2.0).

Example 4

Preparation of a Silane-Functional Monodendron Intermediate

Preparation of trimethyl[3,3″,5,5″-tetrakis(5″-decyl-2,2′:5′,2″-terthien-5-yl)-1,1′:3′,1″-terphenyl-5′-yl]silane (X): A 100 ml three-neck flask provided with magnetic stirrer, reflux condenser, protective gas inlet and septum is charged under $N_2$ gas with (3,5-dibromophenyl)trimethylsilane (215 mg, 0.7 mmol), and $Pd(PPh_3)_4$ (170 mg, $1.5 \times 10^{-4}$ mol) is then added in a glove box. The glass apparatus is assembled and taken from the glove box. Solutions of the compound (IX) (1.47 g, 1.5 mmol) in 30 ml of toluene and $Na_2CO_3$ (2 M aq. (aqueous), 10 ml) are then prepared and deoxygenated by passing $N_2$ through them. The solutions are introduced into the reaction vessel and the reaction mixture is refluxed under $N_2$ gas for 36 hours. The reaction mixture is subsequently cooled to room temperature and poured into a flask containing 100 ml of water and 300 ml of $CH_2Cl_2$. The organic phase is separated off and the aqueous phase is washed with 100 ml of $CH_2Cl_2$. The combined $CH_2Cl_2$ phases are washed with water, dried over $MgSO_4$ and evaporated. The product is purified by repeated crystallization from 4:1 mixtures of hexane/chloroform to give 763 mg of pure product in the form of a brown solid. Yield: 59%. Melting point: 158° C. GPC (polystyrene standard): MP=1540. $^1$H NMR (400 MHz, $CDCl_3$, TMS/ppm): 0.421 (s, 9H), 0.882 (t, 12H, J=7.1), 1.20–1.45 (overlapping peaks, 56 H), 1.684 (m, 8H, M=5, J=7.6), 2.792 (t, 8H, J=7.6), 6.684 (d, 4H, J=3.9), 6.992 (d, 4H, J=3.4), 7.012 (d, 4H, J=3.9), 7.117 (d, 4H, 3.9), 7.179 (d, 4H, 3.4), 7.369 (d, 4H, 3.4), 7.753 (d, 4H, J=1.5), 7.802 (d, 2H, J=1.5), 7.816 (t, 2H, J=1.5), 7.865 (t, 1H, J=1.7).

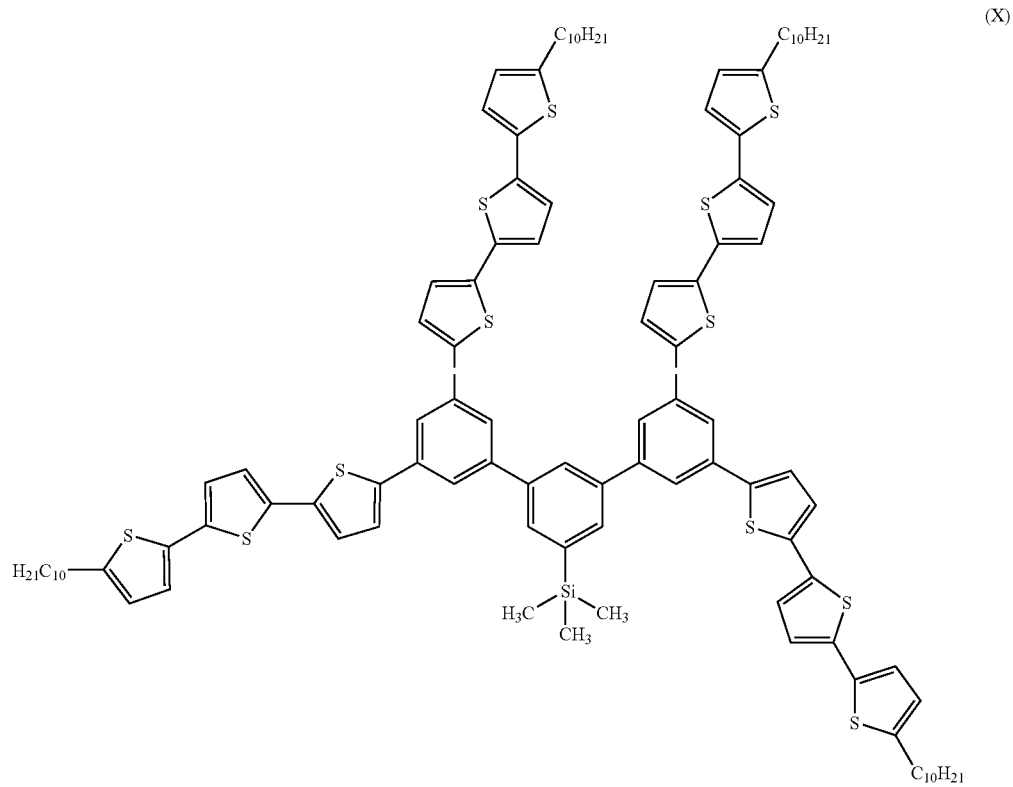

(X)

Example 5

Preparation of a Boron-Functional Monodendron Intermediate

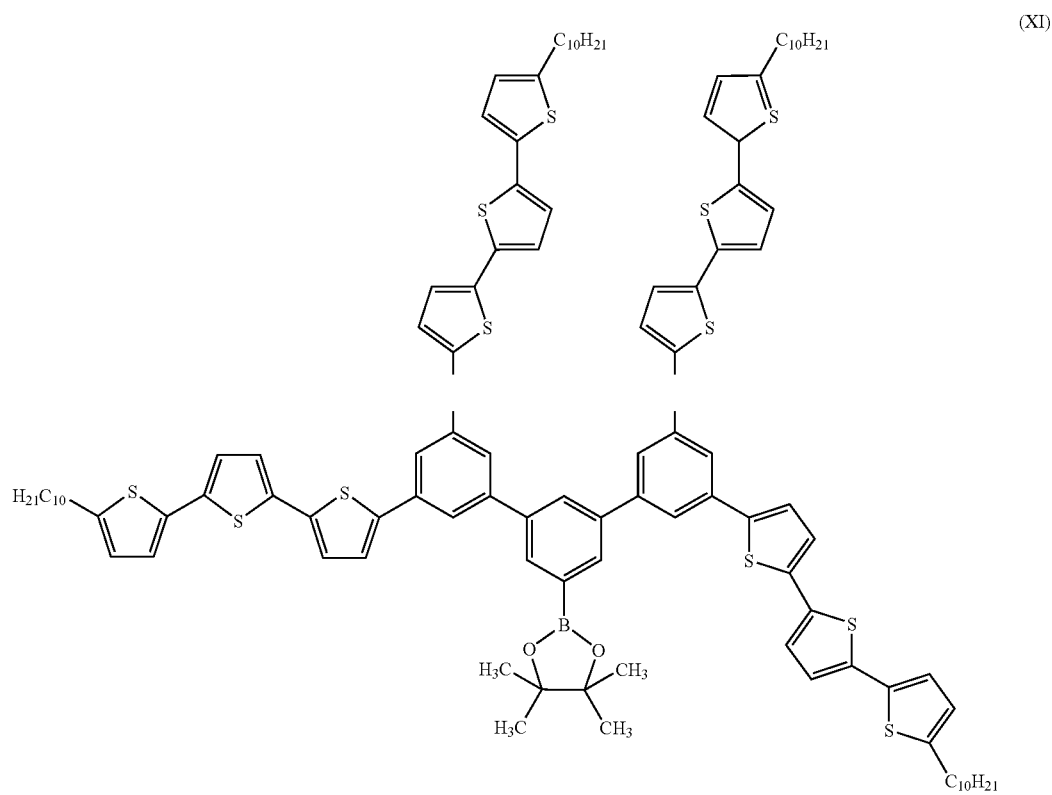

Preparation of 4,4,5,5-tetramethyl-2-[3,3″,5,5″-tetrakis(5″-decyl-2,2′:5′,2″-terthien-5-yl)-1,1′:3′,1″-terphenyl-5′-yl]-1,3,2-dioxaborolane (XI): The compound is prepared from the compound (X) (610 mg, 0.33 mmol), 2 ml of 1M $BBr_3$ solution in tetrachloromethane and pinacol (44 mg, 0.37 mmol) using a process comparable to that described in Example 3. Washing procedures as described in Example 3 and drying under reduced pressure give 650 mg of crude product in the form of a brown solid. After purification by means of column chromatography (eluant: toluene) 310 mg of clean product are obtained as yellowish brown crystals. Yield: 49%. $^1$H NMR (400 MHz, CDCl$_3$, TMS/ppm): 0.882 (t, 12H, J=7.1), 1.20–1.45 (overlapping preaks, 56 H), 1.683 (m, 8H, M=5, J=7,6), 2.790 (t, 8H, J=7.6), 6.682 (d, 4H, J=3.4), 6.987 (d, 4H, J=3.4), 7.001 (d, 4H, J=3.9), 7.112 (d, 4H, 3.9), 7.175 (d, 4H, 3.9), 7.374 (d, 4H, 3.9), 7.785 (d, 4H, J=2.0), 7.799 (t, 2H, J=1.7), 7.988 (t, 1H, J=1.7), 8.123 (d, 2H, J=1.5).

Example 6

Example of the Preparation of a Compound According to the Invention

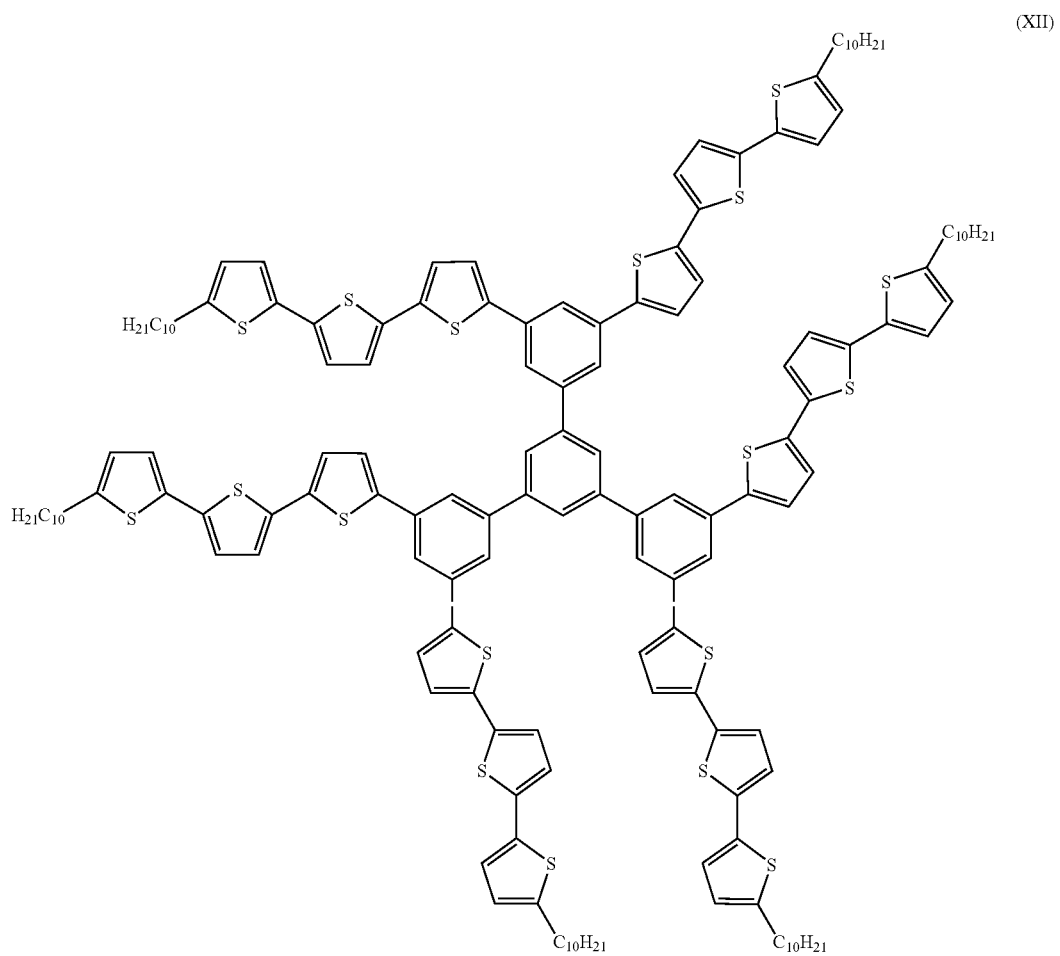

(XII)

Preparation of 1,3,5-tris[3,5-bis(5''-decyl-2,2':5',2''-terthien-5-yl)phenyl]benzene (XII): The compound is prepared from the compound (IX) (450 mg, $4.6 \times 10^{-4}$ mol), 1,3,5-tribromobenzene (40 mg, $1.27 \times 10^{-4}$ mol) and $Pd(PPh_3)_4$ (17 mg, $1.5 \times 10^{-5}$ mol) using a process comparable to that described in Example 4. After refluxing for 16 hours under $N_2$ gas, a yellow solid precipitates as main product. The reaction mixture is cooled to room temperature and poured into 100 ml of water and 400 ml of $CH_2Cl_2$. The organic phase containing the yellow precipitate is washed with three 100 ml portions of water, filtered through a G3 glass filter and the residue on the filter (the product) is washed with three 20 ml portions of $CH_2Cl_2$. Drying overnight in a high vacuum gives 330 mg of the clean product. Yield: 99%. melting point: 202° C.

Example 7

Preparation of a Compound According to the Invention

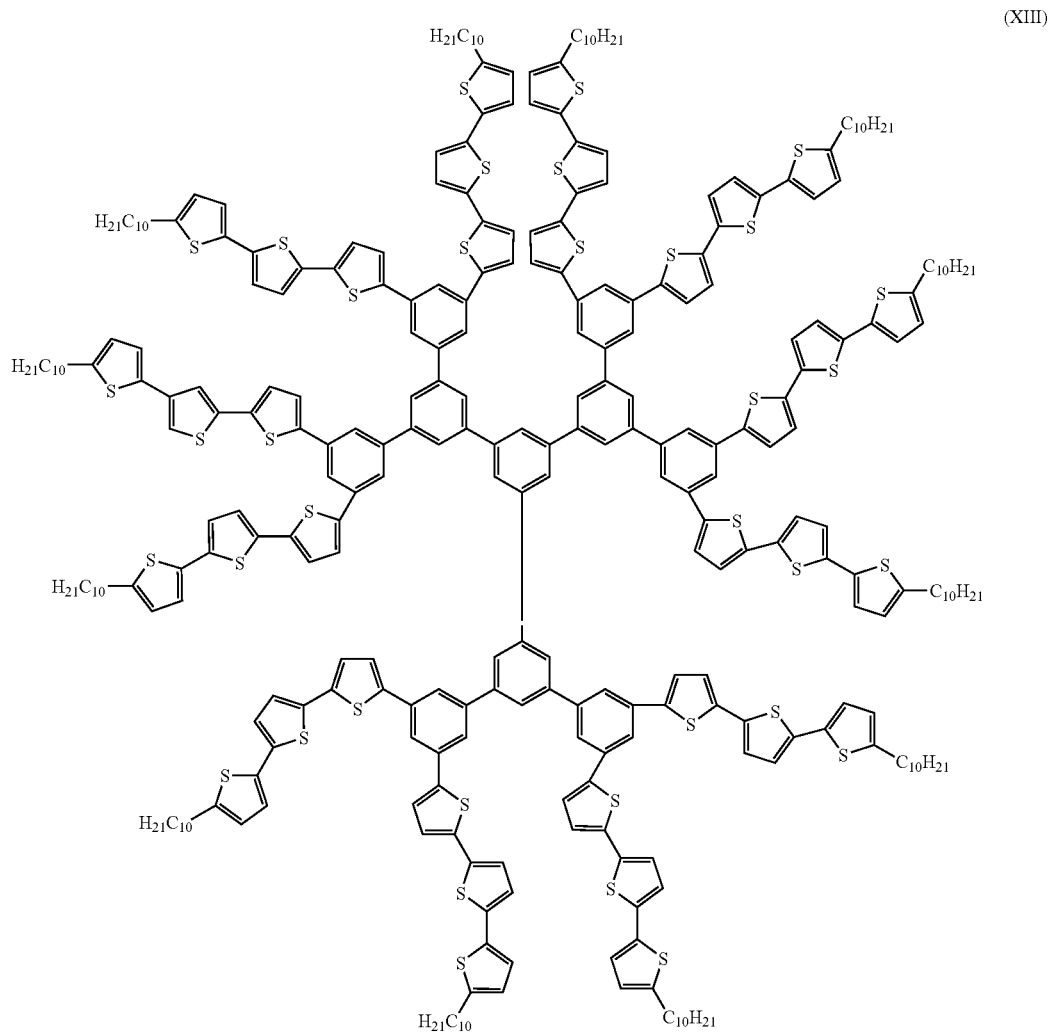

(XIII)

Preparation of 1,3,5-tris[3,3'',5,5''-tetrakis(5''-decyl-2,2':5',2''-terthien-5-yl)-1,1':3',1''-terphenyl-5'-yl]benzene (XIII): The compound is prepared from the compound (XI) (250 mg, $1.3 \times 10^{-4}$ mol), 1,3,5-tribromobenzene (12 mg, $3.8 \times 10^{-5}$ mol) and $Pd(PPh_3)_4$ (10 mg, $8.7 \times 10^{-6}$ mol) using a process comparable to that described in Example 4. After refluxing for 24 hours under $N_2$ gas, the compound is isolated by the procedure described in Example 4. 275 mg of the crude product in the form of a brown solid are purified by means of column chromatography (eluant: toluene) and 210 mg of the clean product are obtained as a brown vitreous solid. Yield: 76%. GPC (polystyrene standard): MP=6900, DPI=1.02.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A compound comprising a core-shell structure comprising,
   (i) a core of multifunctional units, and
   (ii) a shell of linear conjugated oligomeric chains each consisting of a terminal capping group of a flexible nonconjugated chain, wherein, said core-shell structure of said compound is represented by the following formula (Z),

(Z)

wherein

K represents said core having a functionality of n,

L represents said linear conjugated oligomeric chain, said linear conjugated oligomeric chain being selected from the group consisting of representative formulas (VI-a), (VI-b) and (VI-c),

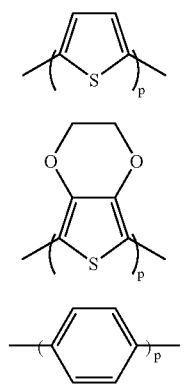

wherein p in each case is 2 to 10, p being the same for each n linear conjugated oligomeric chain L, R represents the flexible nonconjugate chain of said terminal capping group, and is selected from the group consisting of a straight-chain or branched $C_2$–$C_{20}$-alkyl radical, a monounsaturated or polyunsaturated $C_2$–$C_{20}$-alkenyl radical, a $C_2$–$C_{20}$-alkoxy radical, a $C_2$–$C_{20}$-aralkyl radical, a $C_2$–$C_{20}$-oligoether or $C_2$–$C_{20}$polyether radical, and a -$C_{10}H_{21}$ radical, and n is an integer greater than or equal to 3.

2. The compound of claim 1, wherein the core comprises dendritic structures.

3. The compound of claim 2, wherein the core contains 1,3,5-phenylene units as dendritic structures.

4. The compound of claim 1, wherein the core comprises hyperbranched structures.

5. The compound of claim 4, wherein the core contains a hyperbranched polymer as hyperbranched structure.

6. The compound of claim 1, wherein said linear oligomeric chain of the shell is selected from the group consisting of representative formulas (VI-a) and (VI-b).

7. The compound of claim 1, wherein p is 2 to 7 units.

8. The compound of claim 1, wherein the $C_2$–$C_{20}$-alkyl radicals are selected from the group consisting of n-hexyl, n-decyl and n-dodecyl radicals, and the $C_2$–$C_{20}$-alkoxy radicals are selected from the group consisting of n-hexyl, n-decyl or n-dodecyl alkoxy radicals.

9. The compound of claim 1, wherein said compound forms mesophases at temperatures in the range from 50° C. to 300° C.

10. The compound of claim 1, wherein said compound is semiconductive.

11. The compound of claim 1, wherein said compound has a mobility value of at least $10^{-4}$ $cm^2/Vs$.

12. An electronic component comprising the compound of claim 1 as a semiconductor.

13. The compound of claim 1 wherein R is selected from the group consisting of $C_2$–$C_{20}$-polyether radical and —$C_{10}H_{21}$ radical.

14. The compound of claim 1 wherein R is a $C_2$–$C_{20}$-polyether radical.

15. The compound of claim 1 wherein said compound is prepared by a method comprising, (a) preparing said core, (b) preparing said linear conjugated oligomeric chain separately from said core, and attaching said terminal capping group to said linear conjugated oligomeric chain, thereby forming a capped linear conjugated oligomeric chain, and (c) attaching said core and said capped linear conjugated oligomeric chain together.

* * * * *